United States Patent [19]
Vilsmeier et al.

[11] Patent Number: 5,628,315
[45] Date of Patent: May 13, 1997

[54] DEVICE FOR DETECTING THE POSITION OF RADIATION TARGET POINTS

[75] Inventors: Stefan Vilsmeier, Poing; Stefan Lippstreu, Markt Schwaben; Michael Bertram, Heimstetten, all of Germany

[73] Assignee: BrainLAB Med. Computersysteme GmbH, Poing, Germany

[21] Appl. No.: 526,772

[22] Filed: Sep. 11, 1995

[30] Foreign Application Priority Data

Sep. 15, 1994 [DE] Germany .............. 44 32 890.7

[51] Int. Cl.⁶ .................................. A61R 17/00
[52] U.S. Cl. .............. 128/653.1; 128/897; 606/130
[58] Field of Search .................. 128/653.1, 897; 606/130

[56] References Cited

U.S. PATENT DOCUMENTS

| | | |
|---|---|---|
| 4,341,220 | 7/1982 | Perry . |
| 4,535,782 | 8/1985 | Zoltan . |
| 5,147,372 | 9/1992 | Nymark . |
| 5,388,580 | 2/1995 | Sullivan et al. . |
| 5,423,832 | 6/1995 | Gildenberg . |

*Primary Examiner*—Marvin M. Lateef
*Assistant Examiner*—Shawna J. Shaw
*Attorney, Agent, or Firm*—Dann, Dorfman, Herrell & Skillman; Henry H. Skillman

[57] ABSTRACT

The present invention pertains to a device for detecting the position of radiation target points with an anchoring means for attachment to a patient reference system, especially to a stereotactic immobilization system, e.g., a head ring, and with a labeling means, arranged on the anchoring means, for at least one point of coordinates in various three-dimensional projections, in which case the labeling means consists of several computer-printed surface materials, which plot the point of coordinates in a three-dimensional manner.

7 Claims, 4 Drawing Sheets

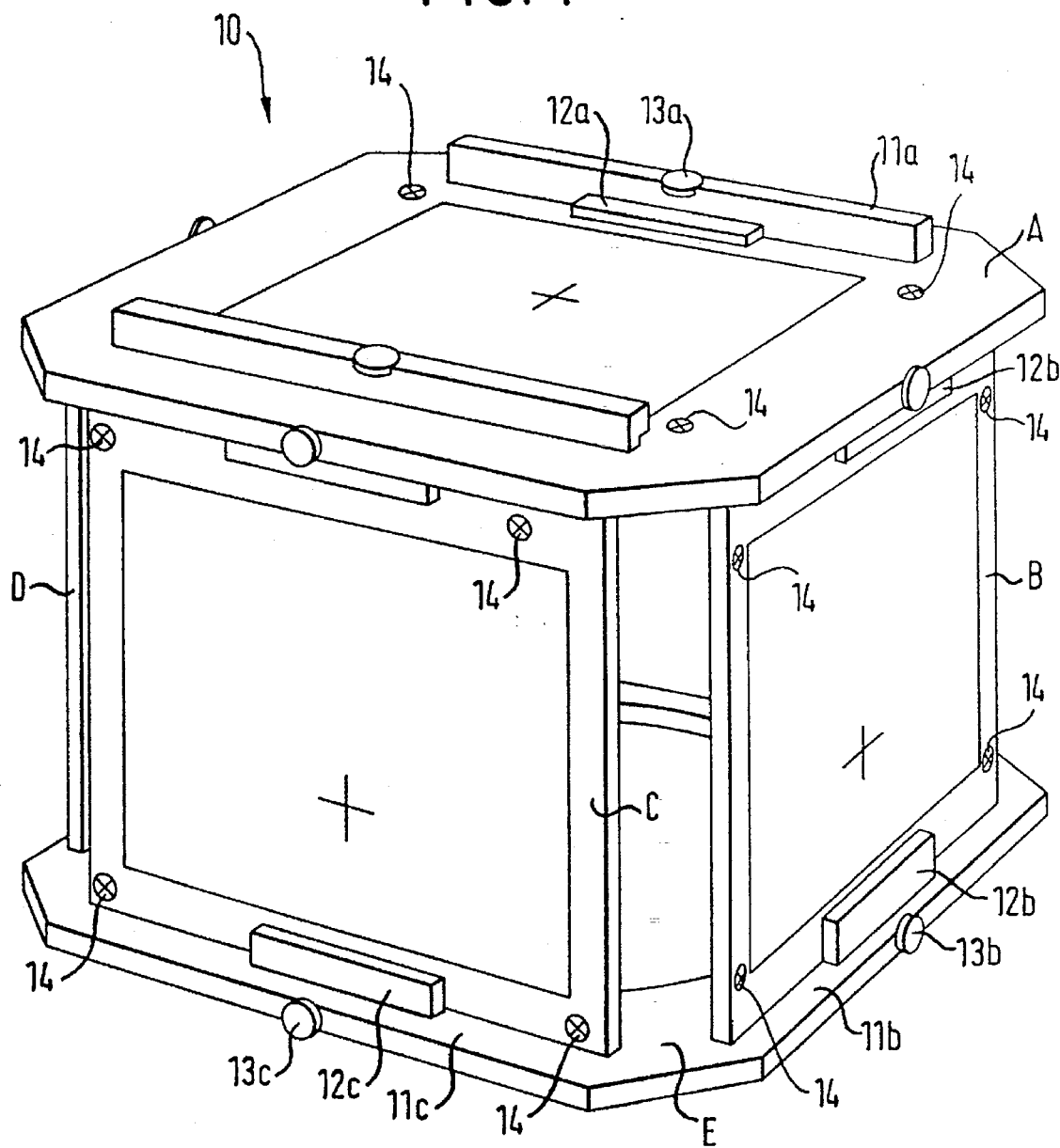

5,628,315

DEVICE FOR DETECTING THE POSITION OF RADIATION TARGET POINTS

FIELD OF THE INVENTION

The present invention pertains to a device for detecting the position of radiation target points for use with a patient reference system, for example a stereotactic immobilization system.

BACKGROUND OF THE INVENTION

Especially brain tumors or vascular deformities are among the diseases which are treated by radiation therapy; even functional targets are radiated. Conventional, invasive, neurosurgical treatment methods are not applicable for all indications, and moreover, they bring with them the disadvantage that a risk of damage to the healthy sections surrounding the focus of the disease frequently arises.

Radiation therapy is an accepted therapeutic method for these diseases, since there is a proven relationship of its action with a therapeutic effect in the patient. E.g., a brain tumor, but also other diseased parts of the body can be treated by means of a linear accelerator. Of course, an exact localization of the diseased sections, of the tumor in this example, is first necessary for this purpose. This localization can be carried out by means of computerized tomography, in which case the patient wears a reference system, usually a head ring in the case of brain tumors, already during the tomography. By precisely localizing and detecting the shape of the tumor, the possibility of reducing the radiation dose on normal tissue presents itself, while, simultaneously, the diseased tissue can be treated with a desired higher dose. With the evaluation of the tomography data, the exact location of the tumor in relation to the reference system is plotted by using three axes of coordinates. The position of the radiation target point, the so-called isocenter, in the tumor is also calculated here. In some cases, it may also be necessary to plot two isocenters.

After the position of the tumor and of the radiation target point is now certain relative to a reference system, which remains on the head or can be arranged again with high accuracy in a reproducible manner, it is necessary to label at least the isocenter for the radiation, so that the isocenter can be hit and treated with the beam of a linear accelerator.

According to the current state of the art, an anchoring means is placed onto the reference system, i.e., the head ring, for this purpose. This anchoring means can have, e.g., the shape of a right parallelepiped consisting of only the lateral edges, which, if it is arranged on the reference system, surrounds the head of the patient. In this case, intermediate mils are, however, arranged between two lateral edges of the right parallelepiped, which are displaceable and adjustable on scales along these lateral edges and thus make it possible for a labeling means, e.g., a prism-shaped body, to be adjusted with the accuracy of the scales on a point of the corresponding surfaces.

A great disadvantage of this device described above concerns the relative inaccuracy with which the projection of the isocenter is adjusted to the respective lateral surfaces of the anchoring means using the scales. This adjustment is made manually and cannot, naturally, exceed the accuracy of the scale (ca. 0.5 mm). However, the exact plotting of the isocenter is very significant particularly for radiation therapy, since damage to the healthy areas surrounding the tumor is to be absolutely avoided.

Another great disadvantage of the prior-art device lies in the fact that the transfer of the data obtained from the tomography to the scale system requires a manual step, in which there is the high risk that the coordinates obtained will be mixed up during the adjustment. In the worst case, such a mix-up can lead to healthy areas of the brain being radiated and thus damaged, in which case, if critical structures are radiated, this can lead to permanent damage in the ability to see or to speak and even to the death of the patient.

Other disadvantages concern the relatively poor clarity of this positioning method, which hardly permits a visual examination of the correctness of the labeling point, and the difficulties in identifying additional data, e.g., the shape of the tumor in the outline. It is also hardly possible to adjust several projections of radiation centers on this device.

SUMMARY OF THE INVENTION

The task of the present invention is to make available a device for detecting the position of radiation target points, which overcomes the above-described disadvantages of the state of the art. An exact and reliable positioning of one or more radiation points should especially be made possible.

This task is solved by an improved device for detecting the position of radiation target points, which comprises an anchoring means adapted to be attached to a patient reference system and labelled with multiple three-dimensional computer-printed projections to determine at least one radiation target point.

The advantage of forming the labeling means, in a device according to the present invention, from several computer-printed surface materials, which plot the point of coordinates in a three-dimensional manner, lies first in the fact that the data obtained from computerized tomography can be transferred, in their converted form, as positioning coordinates projected onto a surface. In this case, it is possible to reach an accuracy of 0.1 mm. This is especially a very significant improvement with regard to the prevention of damage to healthy areas. It is also possible, by means of a computer-controlled production of the projection of the point of coordinates onto surface materials, to arrange several radiation target points on one piece of surface material, if the shape of the diseased section makes this necessary.

A second advantage, which is almost rated even higher, of the device, which is designed according to the present invention, lies in the fact that a manual step in the plotting of the coordinates, which is required in the device according to the state of the art, is eliminated. The risky source of error, which a mix-up of the coordinates when adjusting the target point represents, is ruled out according to the present invention by the fact that, by means of the automatic printing of the surface materials by the computer, which receives its data from the tomographs, the target point projections, which are printed with the corresponding correct coordinates, are also printed onto the corresponding correct surface materials, which can be labeled, in this case, at the same time by the computer so that any error in their arrangement is ruled out.

Many possibilities present themselves here to completely rule out errors in the positioning of the surface materials on the anchoring means. Therefore, it can be guaranteed that only diseased areas are actually treated, and healthy areas are protected from a dangerous concentration of radiation.

In an embodiment of the device according to the present invention, the anchoring means has a rectangular, cubic or right-parallelepiped-shaped housing that is open on one side and has holding fixtures on the lateral surfaces for the computer-printed surface materials. The proven system of designing an anchoring means as described above may thus also be very readily transferred to a device according to the present invention, in which case the material for the anchoring means can be selected from suitable light, but stable materials.

The surface materials used according to the present invention are preferably films with computer-printed labelings of coordinates projected onto the respective surface. The films are printed without distortion by means of a computer printer and permit the patient to still observe his surroundings even with the anchoring means placed on a reference system, which has a favorable effect especially for patients, who are susceptible to claustrophobia.

In addition, it is also possible to plot the outlines of the body to be radiated, for example, of a tumor, which greatly increases the clarity for the attending physicians and furthermore provides a further visual inspection of the correct adjustment of the radiation target point.

Each of the holding fixtures and the associated pieces of surface material are preferably provided with positioning labels that are suitable for one side of the housing. These positioning labels can be arranged such that the positioning labels of the holding fixtures and of the pieces of surface material coincide with one another only on the correct side of the anchoring means, such that, in this manner, already with due care, it can be ruled out that an incorrect piece of surface material can be inserted into a holding fixture. A systematic treatment of the patient is hereby guaranteed.

In an especially preferred embodiment of the device according to the present invention, the holding fixtures and the computer-printed surface materials are designed such that, in each case, only the piece of surface material associated with a holding fixture can be inserted into this holding fixture. In this case, the size and shape of the holding fixtures and of the pieces of surface material can be designed for each side of the anchoring means used such that it is impossible to insert a piece of surface material into an incorrect holding fixture and thus to risk errors in treatment. Thus, an improper radiation based on the mix-Up of labeling points of coordinates can be prevented at a rate of reliability of up to 100%.

BRIEF DESCRIPTION OF THE INVENTION

For the further description of the device according to the present invention, reference is now made to the attached sheets of figures, in which:

FIG. 1 shows a perspective view of an anchoring means according to an embodiment of the present invention;

DESCRIPTION OF THE PREFERRED EMBODIMENTS

Figure 2A:
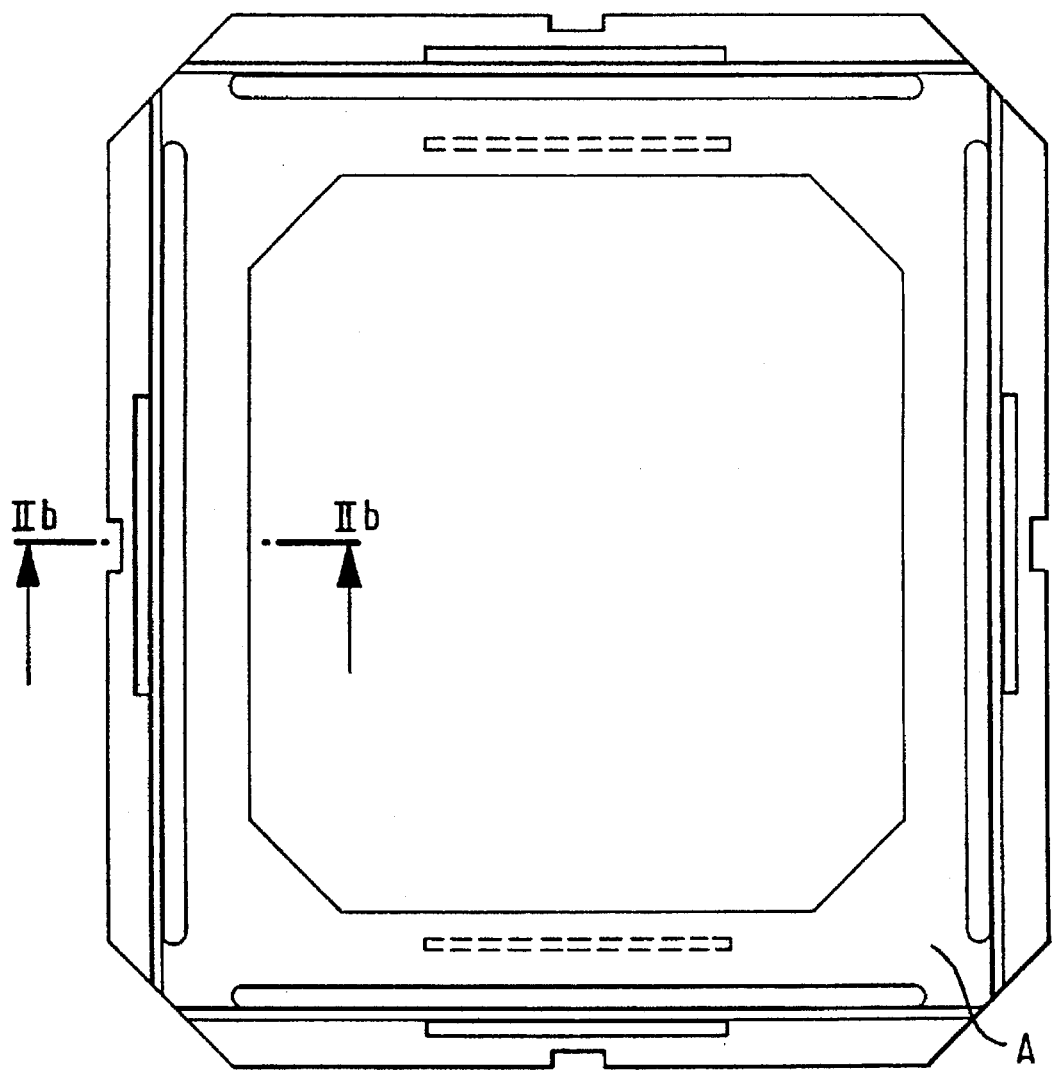
FIG. 2a shows a plan view of the upper plate of an anchoring means.

In the perspective view of FIG. 1, an anchoring means is indicated, as a whole, with the reference number 10. Its lower side E is provided with a cutout section for the head. The anchoring means 10 is attached to a fixed reference system, e.g., a head ring, such that the front side, designated by C, comes to lie above the facial region of the patient. Holding fixtures and guides for the computer-printed surface materials, films in this case, are shown on the upper side A, the front side C and the two lateral surfaces B and D; whereby the side D, which lies opposite the side B, is not visible in the perspective view of FIG. 1.

To guide and attach the computer-printed surface materials, two guide rails 11a, as well as two clamp attachment means 12a which can be clamped and released by means of screws 13a, are provided on the upper side A. On the sides B, C and D, the projections, which project above the plates, of the upper plate A and of the bottom plate E, assume the function of the guide rails, which are arranged on the upper plate A. The clamp attachment means 12b and 12c, which are used to hold the computer-printed surface materials by means of their screws 13b and 13c, are also arranged on these projections in the middle and on both sides.

As a result, it is obvious that the point of coordinates to be plotted, with which the tumor is localized, is labeled on four surfaces with two projection points in each case. A total of eight coordinate values are therefore available for a point plotted three-dimensionally with three coordinate values. Thus, with the computer-printed films applied, a visual inspection of the correct arrangement of the labeling points can again be carded out by means of this agreement.

Four positioning labels 14, crosses dram in a circle in this case, are provided on the front side C. The computer-printed film assigned to this side has the same type of positioning labels drawn in the same position as well, so that, if all labels coincide with one another when the film is arranged and clamped, it can be assumed from this that the film is arranged correctly, and the radiation target point is correctly plotted in the position of this side. The positioning labels are arranged in a different manner on each of the sides, so that, therefore, no mix-up is possible in the films, because an incorrect computer-printed film may not be arranged on a side not associated with it, so that the cross labels coincide.

The principle of attachment of this embodiment of the present invention becomes even more evident from FIG. 2a, which shows an upper plate of the device according to the present invention, FIG. 2a is a partial view of the attachment mechanism, i.e., of the clamps 12a, the guides mils 11a and the screws 13a. The guide rail 11a is inserted into a groove 16 in the upper plate A. In the middle of this guide rail, a screw 13a, here a knurled screw, is screwed into a thread in the guide rail and, with its lower surface, presses from above onto an attachment clamp 12a, by means of which this clamp 12a is able to clamp and position a computer-printed film on the upper surface of the side A together with the opposite attachment means.

As is also evident, the part 11C of the plate A, which projects above the plate C, is used as a guide rail for a computer-printed film to be arranged on the side C. The attachment means of the side C, which also consists of a knurled screw 13c and a clamp 12c, is otherwise similar in terms of function and action to that of the upper side A.

By means of using unique indicia respectively on the holding fixtures and the surface materials e.g., edges arranged differently on each side in the guide rails, or similar shaping measures, it is very readily possible in the present embodiment of the present invention to design the guides or the plates, such that only the indicia of the associated computer-printed film can register with indicia of the respective side A, B, C or D in each case. Thus, in a simple manner, a very reliable system is provided for plotting radiation target points.

Figure 3:
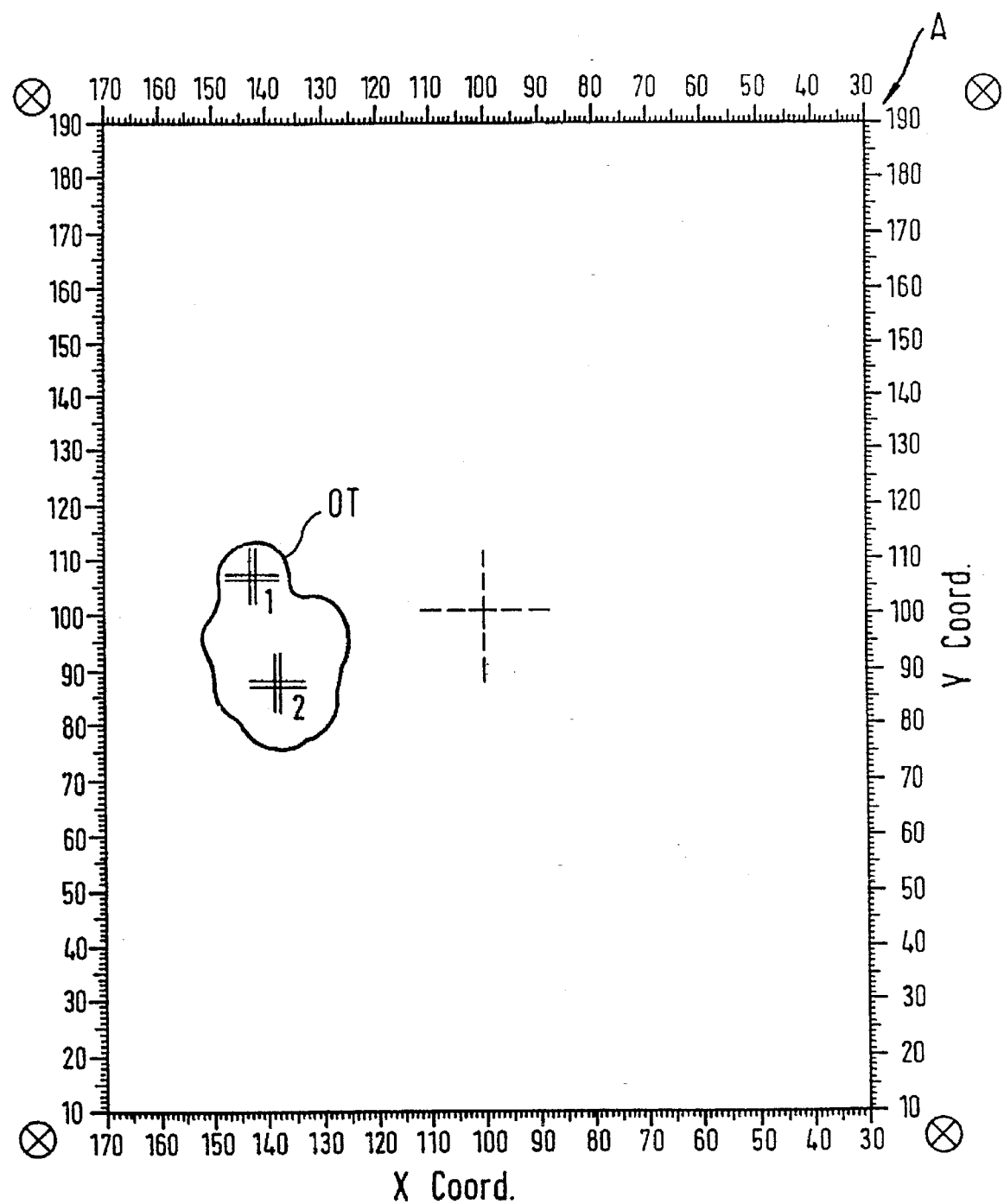
FIG. 3 shows an example of a computer-printed film to be inserted into a holding fixture.

FIG. 3 shows a photocopy of a film to be inserted into a holding fixture of side A. The film is provided with the designation A for the lateral surface A and with positioning labels, also crosses drawn in a circle here, which are to be coincided only upon the correct insertion of the film into the holding fixture with the labelings found there. A system of coordinates, consisting of X and Y coordinates, is mounted rectangularly on the film.

Figure 4:
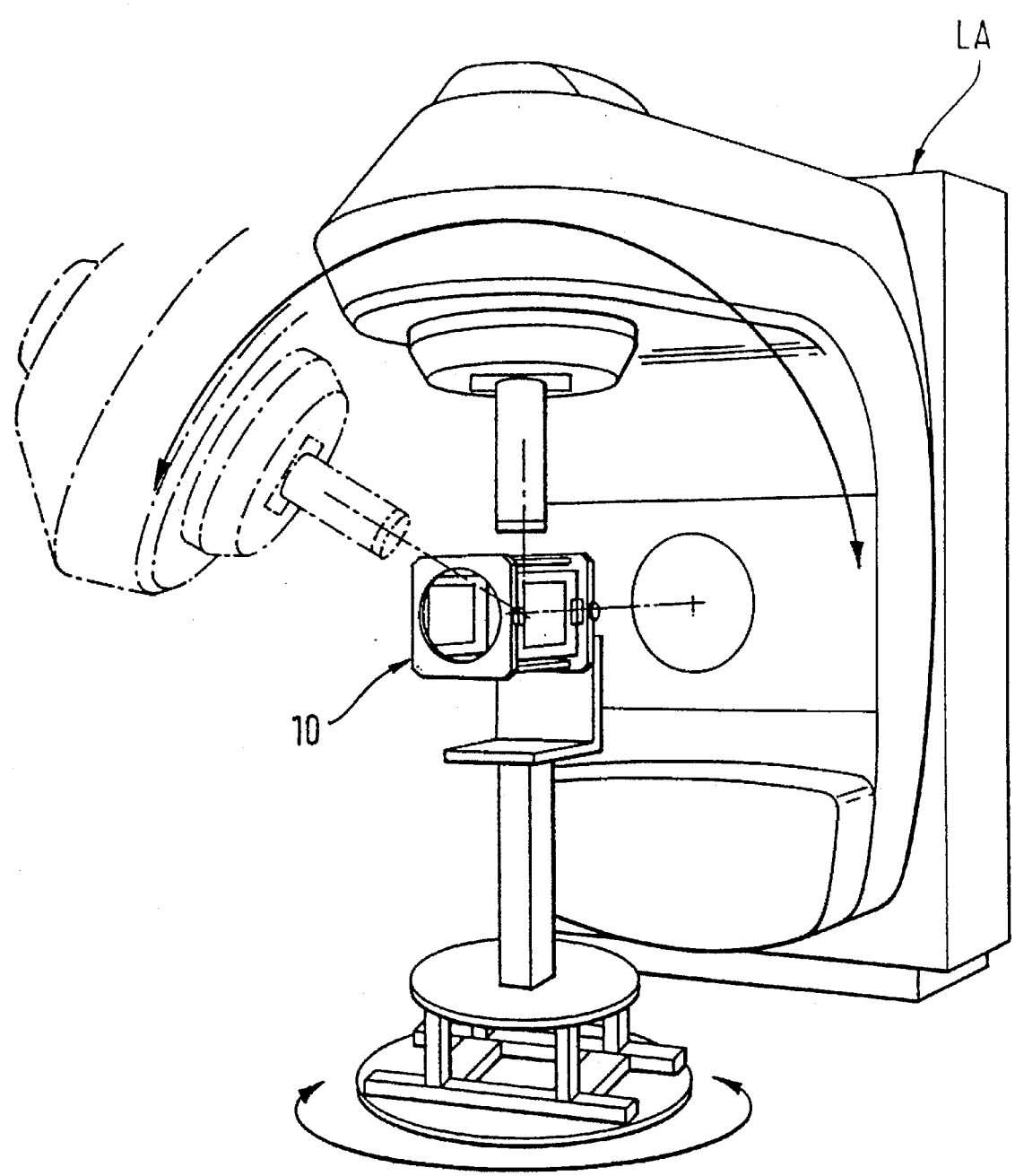
FIG. 4 shows a perspective view of the anchoring means in use with a linear accelerator.

With the dam obtained from the computerized tomography, two isocenters 1 and 2 are labeled with crosses as projections onto this surface, so that the target point can be detected here by means of the beam of the linear accelerator LA (see FIG. 4) with the accuracy of the computer printout. To improve the clarity and to make possible a further visual inspection by the attending physicians, the outlines of the tumor to be treated, detected by the computer, are also printed on the film.

The films for the other lateral surfaces B, C and D are designed correspondingly and are provided with labelings and outlines.

It should be mentioned once again that the device according to the present invention is not limited to the treatment of diseases in the brain. All diseases, even of other parts of the body, to be treated with radiation therapy can be treated with a device according to the present invention by means of correspondingly designed anchoring means and reference systems.

We claim:

1. Device for detecting the position of radiation target points in a body to be radiated while in a patient reference system, said target points having defined coordinates relative to said system, said device comprising an anchoring means for attachment to the patient reference system, and a labeling means, arranged on the anchoring means, for said defined coordinates of at least one target point in various three-dimensional projections, said labeling means comprising several computer-printed surface materials, which plot the defined coordinates of said target point in a three-dimensional manner.

2. Device in accordance with claim 1, said anchoring means having a rectangular, cubic or right-parallelepiped-shaped housing, which is open on one side and providing a plurality of lateral surfaces on other sides, and holding fixtures for the computer-printed surface materials on the lateral surfaces.

3. Device in accordance with claim 1 wherein the surface materials are films with computer-printed coordinate labelings projected onto the surface material.

4. Device in accordance with claim 1 including printed outlines of the body to be radiated on the surface materials.

5. Device in accordance with claim 2, said holding fixtures and the associated surface materials of the labeling means are each provided with positional labels which may be registered with only one side of the housing.

6. Device in accordance with claim 5, wherein said positional labels of the holding fixtures and the computer-printed materials respectively comprise unique indicia adapted to register with each other, such that, in each case, only the surface material associated with one holding fixture can be inserted into said one holding fixture.

7. Device according to claim 1 wherein said surface materials are transparent to the radiation to be applied to said target point, whereby said labeling means are adapted to be used to direct said radiation to said target point.

* * * * *

UNITED STATES PATENT AND TRADEMARK OFFICE
CERTIFICATE OF CORRECTION

PATENT NO. : 5,628,315

DATED : May 13, 1997

INVENTOR : Stefan Vilsmeier et al.

Figure 2B:
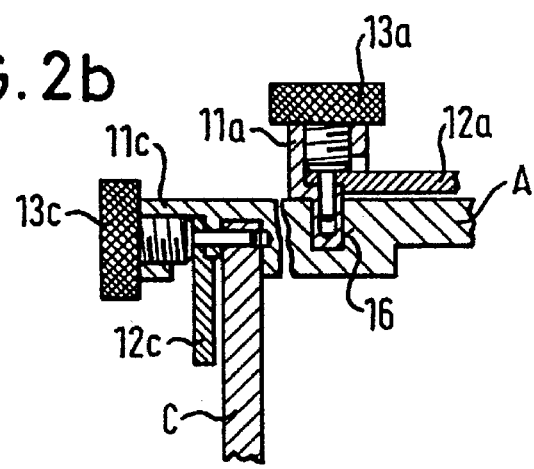
FIG. 2b is a partial cross section taken on the line IIb—IIb of FIG. 2a which shows the attachment means for the computer-printed surface materials.

It is certified that errors appear in the above-identified patent and that said Letters Patent is hereby corrected as shown below:

Column 1, line 51, "mils" should be --rails--;

Column 3, line 40, "mix-Up" should be --mix-up--;

Column 4, line 42, "Fig. 2a" should be --"Fig. 2b--;

line 43, "mils" should be --rails--;

Column 5, line 9, "dam" should be --data--.

Signed and Sealed this

Twenty-third Day of December, 1997

Attest:

BRUCE LEHMAN

*Attesting Officer*      *Commissioner of Patents and Trademarks*